United States Patent [19]

Kruse et al.

[11] Patent Number: 4,767,559
[45] Date of Patent: Aug. 30, 1988

[54] PROCESS FOR PRODUCING CONTACT LENS CLEANING TABLETS WITH A DISINFECTING ACTION FOR ONE-STEP CLEANING

[75] Inventors: Hans Kruse, Korschenbroich; Jochen Jacobs, Wuppertal; Klaus-Dieter Wisotzki, Erkrath; Jutta Thul, Hilden, all of Fed. Rep. of Germany

[73] Assignee: Henkel Kommanditgesellschaft auf Aktien, Duesseldorf, Fed. Rep. of Germany

[21] Appl. No.: 35,848

[22] Filed: Apr. 8, 1987

[30] Foreign Application Priority Data

Jan. 16, 1987 [DE] Fed. Rep. of Germany ....... 3701129

[51] Int. Cl.⁴ .................. C11D 7/42; C11D 7/54; A61L 2/16
[52] U.S. Cl. ..................................... 252/106; 252/90; 252/95; 252/174; 252/174.12; 252/174.13; 252/176; 252/DIG. 12; 427/3; 424/482
[58] Field of Search .................... 252/174.12, 174.13, 252/DIG. 12, 106, 90, 95, 174, 176; 427/3; 424/14, 31

[56] References Cited

U.S. PATENT DOCUMENTS

| | | | |
|---|---|---|---|
| 4,155,868 | 5/1979 | Kaplan et al. | 252/95 |
| 4,285,738 | 8/1981 | Ogata | 134/26 |
| 4,388,229 | 6/1983 | Fu | 252/549 |
| 4,414,127 | 11/1983 | Fu | 252/95 |
| 4,500,441 | 2/1985 | Tanaka et al. | 252/89.1 |
| 4,568,517 | 2/1986 | Kaspar et al. | 422/30 |
| 4,585,488 | 4/1986 | Giefer | 134/27 |
| 4,614,549 | 9/1986 | Ogunbiyi et al. | 134/19 |
| 4,670,178 | 6/1987 | Huth et al. | 252/95 |

FOREIGN PATENT DOCUMENTS 3329922 2/1985 Fed. Rep. of Germany .
86/05695 10/1986 PCT Int'l Appl. .

*Primary Examiner*—Paul Lieberman
*Assistant Examiner*—Ronald A. Krasnow
*Attorney, Agent, or Firm*—Ernest G. Szoke; Henry E. Millson, Jr.; Mark A. Greenfield

[57] ABSTRACT

Methods for producing a contact lens one-step cleaning and disinfecting tablet designed to be dissolved in water comprising:

(A) preparing a tablettable neutralizing core mixture consisting essentially of at least one biocompatible reducing agent, at least one biocompatible catalyst, and at least one first buffering agent;
(B) forming a core tablet from the mixture of step (A);
(C) preparing a jacket mixture consisting essentially of at least one biocompatible cleaning and disinfecting agent and a second buffering agent; and
(D) enveloping the core tablet of step (B) with the jacket mixture of step (C) so that it is completely surrounded by a stable outer layer thereof, as well as tablets produced by such methods.

32 Claims, No Drawings

PROCESS FOR PRODUCING CONTACT LENS CLEANING TABLETS WITH A DISINFECTING ACTION FOR ONE-STEP CLEANING

BACKGROND OF THE INVENTION

1. Field of the Invention

The increasing number of wearers of soft or hard contact lenses makes it necessary to supply a system of disinfection and cleaning agent which in every case is convenient and safe to use. Peroxy compounds are chiefly used for this purpose; they destroy bacteria and fungi, but excess quantities of these must in turn be destroyed before the lenses are replaced on the pupils.

2. Statement of Related Art

In Canadian Pat. No. 1,099,885 (and corresponding German published patent application No. 28 35 652), for the disinfection and cleaning of contact lenses, a redox system consisting for example of ascorbic acid and an alkali percarbonate which gives a strong alkaline reaction in aqueous solution is used. The contact lenses are placed in this aqueous solution for about 5 min. After disinfection has been performed in this way, the lenses are rinsed with sodium chloride solution, if desired, and then can be replaced in the eyes. The redox system is mixed dry and supplied in moisture-tight packaging as a powder, a granulate, or in tablet form. Nothing is disclosed regarding the nature and production of the tablets.

In accordance with German published patent application No. 33 29 922, contact lenses are disinfected and cleaned by placing them for 10–20 minutes in a solution of sodium chloride with a table (A) of urea peroxyhydrate dissolved in it; after which they are left for 15 minutes in a fresh solution of sodium chloride with a tablet (B) of sodium ascorbate or a mixture of ascorbic acid and sodium carbonate dissolved in it; and finally are placed for at least 5 minutes in a fresh sodium chloride solution. After this complex process, using 2 different tablets, the lenses can again be worn.

In U.S. Pat. No. 4,585,488 (and corresponding European published patent application No. 82,798), a process is described for disinfecting and cleaning contact lenses, according to which they are first placed for about 20 minutes in a hydrogen peroxide solution, to which a commercially available catalase tablet is subsequently added to destroy $H_2O_2$ excesses. The enzyme acts within 5 minutes. Here again the two required agents are introduced separately to the system.

Up to the present time, a disinfection and cleaning agent system has apparently proven most convenient for the user in which, for example, urea peroxohydrate is used in a sodium chloride solution together with a cationic, nonionic or preferably amphoteric or anionic surfactant and a catalyst for the subsequent destruction of the peroxide excess. Such a system is described in U.S. Pat. No. 4,414,127. The separately packaged system constituents likewise described, namely: (A) the urea peroxohydrate; and (B) a solution of the surfactant, the catalyst and the sodium chloride are combined immediately before use, requiring no third step rinse.

Basically, the problem of producing a suitable, reliable, and convenient form of supply of disinfecting cleaners for contact lenses is as yet unresolved, since it is difficult to combine and package together substances which undergo chemical reaction with one another.

DESCRIPTION OF THE INVENTION

Other than in the operating examples, or where otherwise indicated, all numbers expressing quantities of ingredients or reaction conditions used herein are to be understood as modified in all instances by the term "about".

The present invention affords a "jacketed" tablet, in which the outer layer (the jacket) comprises the disinfecting cleaning agent, which first dissolves in water and acts on the contact lenses placed in the solution. Then, after a time delay, the core of the original tablet dissolves, neutralizing excess disinfectant and cleaning agent.

This invention also affords a method for producing disinfecting contact lens cleaning agent tablets, which is characterized in that (1) in a first process step a storage-stable, tablettable core mixture comprising the neutralizing agent is prepared, and (2) a core tablet is made from this in a second process step, which core tablet (3) is preferably but not essentially coated with a lacquer layer in a third process step, before or after which (4) a "jacket" mixture consisting of the actual cleaning agent is prepared in a fourth process step, and finally, (5) the core tablet is pressed into and surrounded by the jacket mixture in a fifth process step.

When these tablets are used, the active ingredients are released in the desired sequence (i.e., in reverse sequence to manufacturing). During manufacturing and storage, almost no losses of activity arise due to premature adverse reactions, and the cleaned contact lenses have been shown not to cause any eye irritations, which can be evaluated as a sign of the complete neutralization of the disinfecting cleaner.

As constituents for the jacket mixture, which exerts a disinfecting and cleaning action, and thus represents the actual cleaning agent, one or more compounds supplying hydrogen peroxide are preferred, to which one or more alkylglucosides are added.

Any known acid-reacting hydrogen peroxide generating biocompatible compound may be used, for example, potassium persulfate, melamine perhydrate and preferably urea peroxohydrate, all of which show an acid reaction in aqueous solution.

As alkylglucosides, those preferred have the general formula $R_1O(C_nH_{2n}O)_y(Z)_x$, wherein $R_1$ is a $C_{8-18}$, preferably $C_{12-14}$ alkyl, n is 2 or 3, y is 0–10, preferably 0, Z is glucose, and x is an average of 1–10, preferably 1–5.

These alkylglucosides, which are themselves surface-active, preferably are combined with one or more additional compatible nonionic surfactants which do not interfere with the performance-enhancing antimicrobial characteristics. Examples of these are fatty alcohol ethoxylates, adducts of ethylene oxide and propylene oxide with fatty alcohols, or fatty alcohol ethoxylates terminating in n-alkyl moieties. The cloud points of the cleaning and disinfection solution are mostly controlled with these surfactants, and their known antifoaming properties may be utilized.

If necessary, other known auxiliaries can also be incorporated into the tablets for foam suppressing, e.g., dimethylpolysiloxanes or modifications thereof, paraffins or hydrophobically treated silicas. Particularly suitable is polysiloxane EH 7566, a product of the Goldschmidt Company. The auxiliaries are present in a foam-dampening-effective amount and, depending on the surfactant content of the cleaning solution, the preferred utilization concentrations in the solution are between 0.01 and 0.0001 weight percent.

When these foam-suppressing auxiliaries are optionally used, the need for compatible nonionic surfactants in addition to the alkylglucoside can be eliminated.

Additional auxiliaries are preferably added to the peroxy compound-containing fraction of the disinfection and cleaning agent system, especially those which establish the pH during cleaning at 2 to 7, preferably 3.5. Any biocompatible acid second buffering agent can be used, citric acid, salicylic acid, lactic acid, or mixtures thereof being preferred. These auxiliaries can also distinctly increase the antimicrobial activity of the solution.

The alkylglucosides are mixed mechanically with the powdered peroxy compounds in a known way, wherein the ratio of the average molecular weights of peroxy compound to alkylglucoside is $1 \cdot 10^2$ to $32 \cdot 10^4:1$, preferably $1 \cdot 10^3$ to $32 \cdot 10^3:1$, and most preferably $1 \cdot 10^3$ to $8.3 \cdot 10^3:1$. Addition of sodium chloride improves the solubility of the jacket layer of the tablets, when added in at least soluble improvement-effective amounts. The core tablet is later surrounded with this jacket layer mixture.

The quantities of generated $H_2O_2$ not used in the disinfection and cleaning process are neutralized by the slightly time-delayed dissolution of the core tablet containing the neutralizing agent, which comprises at least one biocompatible reducing agent and/or at least one catalyst. Suitable reducing agents are, for example, ascorbic acid, sodium ascorbate or glucose. Enzymes are used as the catalysts. A particularly suitable and preferred enzyme is catalase ($H_2O_2:H_2O_2$ oxidoreductase; E.C. 1.11.1.6), which may be obtained from Sigma Chemical Co., among others. The activity of the catalase is given in Sigma units per mg. of protein. Beginning from a concentration of 10.3 micromols/ml in the reaction mixture, at pH 7 and 25° C., one Sigma unit breaks down 1 micromol of $H_2O_2$ per minute. The determination is performed by measuring the rate of decrease in absorption at 240 nm.

If only reducing agents are used during neutralization, excessive heat can evolve, which under certain circumstances can exert a damaging effect on the lenses. If only catalysts, i.e., enzymes, are used, the neutralization of the remaining $H_2O_2$, to be sure, will proceed rapidly, but only at room temperature, and the advantages of heat evolution will be eliminated. Therefore the combination of a reducing agent with an enzyme, preferably catalase, has proven advantageous for neutralization, since the cleaning solution will then be slightly heated when neutralization begins, and the heat therefore will advantageously support the chronological course and the cleaning effect, e.g., with regard to removal of fatty and/or proteinaceous soils.

The quantity of reducing agent when used alone corresponds to that of the peroxy compound used, i.e., equimolar amounts are used with an excess of 1–5, preferably 2–4 mol percent of reducing agent. When it is used together with an enzyme, the quantity of the reducing agent can be decreased by about one quarter to one half of that amount.

Depending on the activity, the enzyme is used in quantities of 0.001–0.2 mg/ml solution, preferably 0.005–0.1 mg/ml solution, based on the quantity of peroxy compound.

In addition to the reducing agent and the enzyme, the neutralizing agent for reducing the $H_2O_2$ residues of the disinfection and cleaning agent system also contains first buffer salts which adjusts the pH value of the overall solution to about pH 7, for example sodium hydrogen carbonate (sodium bicarbonate), sodium carbonate or sodium citrate. If needed the previously mentioned compatible surfactants and/or additional salts such as sodium chloride and/or coloring agents can likewise be present.

It is critically necessary to prevent the reducing agent and/or the enzyme from reacting with the peroxy compound of the jacket layer prematurely, especially during storage. On the other hand the enzyme in the core mixture loses its activity during storage in the presence of other core constituents, especially sodium hydrogen carbonate. To avoid this, the core tablets may be, and preferably are, sealed with a water-soluble lacquer layer. At the same time the enzyme fraction or the remainder of the core mixture also may be enveloped with an acid or neutrally-adjusted lacquer layer.

Any biocompatible, water-soluble substance capable of forming a lacquer layer on the respective substrates may be used, for example polyvinyl acetate, polyvinyl alcohols, polywaxes, polyvinyl pyrrolidone, cellulose ethers and their derivatives, or mixtures thereof, and preferably polyacrylates. It is critical that a sufficient quantity be used so that the coating is continuous. Quantities of about 3–15 weight percent, based on the weight of the substrate to be covered, are generally sufficient for this purpose.

Since premature reactions of the actived substances with one another must be avoided and are promoted by residual water contents, water-binding salts can also be incorporated into the tablets, such as magnesium sulfate or sodium sulfate. The quantities of these salts are minimally sufficient to bind residual water effectively, and amount to up to 15 weight percent, preferably 5–10 weight percent, based on the total weight of the tablets.

The addition of known tabletting aids may also prove advantageous. Physiologically well tolerated polyethylene glycol with an average molecular weight of 6,000 is especially suitable. The application quantities are 1–5, preferably 2–3, weight percent, based on the mixture to be pressed.

In order to prevent a reaction of the jacket composition with liberation of water during storage, it is advisable to store the tablets together with known drying agents, e.g., commercial drying tablets specially developed for such purposes, or under exclusion of humidity from the air.

It should also be noted that "neutralization" in the sense of the application is defined as the destruction of excess $H_2O_2$ and the adjustment of the cleaning agent solution to pH 7. The means used for this are any known biocompatible "neutralizing agents."

EXAMPLES

EXAMPLE 1

Composition of the jacket mixture:
91.86 wt-% urea peroxohydrate (peroxide generator)
0.06 wt-% alkylglucoside from a $C_{12-14}$ fatty alcohol where x=1.4
0.12 wt-% reaction product of $C_{12-14}$ fatty alcohol etherified with n-butanol and 9 mol ethylene oxide (nonionic surfactant)
7.96 wt-% citric acid (second buffer) forming 100% active ingredient, which is cut to 97% active ingredient by adding 3 wt-% sodium chloride. For each tablet, the jacket mixture contains 1.63 g active material.

Composition of the core mixture:

0.10 wt-% catalase (10,000–25,000 units/mg, according to Sigma) (catalyst)
60.08 wt-% sodium ascorbate (reducing agent)
39.53 wt-% sodium hydrogen carbonate (first buffer)
0.30 wt-% reaction product of a $C_{12-18}$ fatty alcohol and 9 mol ethylene oxide (nonionic surfactant)

forming 100% active ingredient, which was cut with an additional 10 wt-% magnesium sulfate. In addition, about 6 wt-% polyacrylate, calculated as solid substance, and 3 wt-% polyethylene glycol with an average molecular weight of 6000 was added as a tabletting aid. The core mixture contained, in each tablet, 0.63 g of the tabletting mass with an active ingredient content of about 80–90%.

The tablets were produced as follows:

1. Production of a Storage-stable, Tablettable Core Mixture

A series of experiments performed earlier had shown that the catalase loses activity in the presence of sodium hydrogen carbonate. Therefore it was first necessary to keep the ingredients from so reacting, one way being to surround the sodium hydrogen carbonate or the catalase-free core mixture with a tight lacquer layer soluble under application conditions. This was performed in a hot air-driven fluidized bed, wherein 6 wt-%, calculated as solid matter, of an aqueous, neutral-adjusted acrylic resin solution (a copolymer based upon polyacrylic acid and polyacrylic acid esters) was sprayed into the fluidized substances using a dual-substance nozzle. The 6.4% acrylic resin solution was also provided with added plasticizer, namely 1.3% triethyl citrate and 1.45% sodium hydroxide.

An even better coating and a subsequently better pressing ability were achieved by using coarser grades of raw materials. For this reason it can be advantageous to use as the starting product coarse commercial granulates, or for example, roller-compacted granulates. The mixing of the nozzle sprayed substance or substances with the remaining components took place in a gentle mixing system. The tabletting aids used were 3 wt-% polyethylene glycol with an average molecular weight of 6000. Addition of 10 wt-% $MgSO_4$ as the drying agent was performed carefully to improve the storage properties of the tablets.

2. Preparation of the Core Tablet

The pressing of the above tabletting mixture was accomplished on a rotary tablet press. The tablets produced were lens-shaped, with a diameter of 10 mm and a height of about 6.5 mm. Stable tablets, able to withstand further treatment, were obtained by empirical optimization of the pressing pressure, which amounted to about 10,000 kilos per square centimeter.

3. Enveloping of the Core Tablets

In order to prevent subsequent reaction of the acid components of the jacket with the alkaline constituents of the core, it is desireable but not necessary to envelop the core tablet itself, likewise with a neutral-adjusted aqueous acrylic resin solution such as used in step 1. This was done in a rotary coating drum. The resin solution was sprayed onto the tablets, kept in motion, through a dual-substance nozzle. At the same time, water which was simultaneously sprayed was evaporated by blowing in air heated to 40° C. The addition rate of the solution was balanced with the air stream in such a way that the sprayed water always evaporated directly and thus the tablets did not stick together. A lacquer application (dry matter) of 3 mg/cm$^2$, based on the weight of the material sprayed, was sufficient.

4. Preparation of the Jacket Mixture

In order to obtain a uniform mixture composition, premixing of the components with a small part of the urea peroxyhydrate, about 5 wt-%, had to be performed. Then this premix was mixed with the remaining fractions of urea peroxyhydrate and citric acid, as well as the added 3 wt-% sodium chloride. The sodium chloride addition improved the solubility of the tablets and the physiological compatibility of the cleaned contact lenses with the eye.

5. Jacketing of the Enveloped Core Tablets

This was done according to the following principle: Enveloped core tablets as described under steps 1–3 were passed over a vibrating container on the transfer disc into the matrix hole on a special rotary tabletting press for producing jacketed tablets, manufactured by Kilian (model RUD), into which a portion of the jacket layer had previously been metered. The approach of the upper piston centered the core tablet in the jacketing composition before the remainder of the jacketing layer was added. This was followed by pressing, wherein perfect binding of the jacket composition with the core was ensured by an accurate empirical adjustment of the pressing pressure.

The tablet produced had a diameter of 16 mm and a height of 10–11 mm. Even after storage at room temperature (with silica gel drying tablets), no loss of activity was noted.

Tablets of the following compositions were also manufactured according to the same principle:

EXAMPLE 2

Composition of the jacket mixture:

91.97 wt-% urea peroxyhydrate (peroxide generator)
0.06 wt-% alkylglucoside ($C_{12-14}$ fatty alcohol where $x = 1.4$) and
7.97 wt-% citric acid (second buffer)

forming 100% active ingredient, which were reduced to 97% active ingredient by addition of 3 wt-% sodium chloride. For each tablet, the jacket mixture contained 1.63 g active substance.

Composition of the core mixture:

0.10 wt-% catalase (10,000–25,000 units/mg according to Sigma) (catalyst)
60.24 wt-% sodium ascorbate (reducing agent)
39.63 wt-% sodium hydrogen carbonate (first buffer) and
0.03 wt-% siloxane EH 7566 (auxiliary)

forming 100% active ingredient, which was also mixed with ca. 6 wt-% polyacrylate, calculated as the solid substance, and ca. 3 wt-% polyethylene glycol with an average molecular weight of 6000 as tabletting aid.

The core mixture contained 0.63 g of the composition per tablet.

EXAMPLE 3

Composition of the jacket mixture:

0.7 wt-% ethylene diamine tetraacetic acid Na salt
90.15 wt-% melamine perhydrate (peroxide generator)
0.07 wt-% alkylglucoside $C_{12-14}$ fatty alcohol where $x = 1.4$
9.08 wt-% citric acid (second buffer)

forming 100% active ingredient, which was reduced to 97% active ingredient by adding 3 wt-% sodium chloride. In each tablet, the jacket mixture contained 1.43 g active ingredient.

Composition of the core mixture:
0.44 wt-% catalase (catalyst)
99.52 wt-% sodium hydrogen carbonate (first buffer)
0.04 wt-% siloxane EH 7566 (auxiliary)
forming 100% active ingredient. In addition, about 6 wt-% polyvinyl pyrrolidone, calculated as the solid substance, and ca. 3 wt-% polyethylene glycol with an average molecular weight of 6000 were added as a tabletting aid.

The core mixture contained 0.26 g of the composition per tablet.

At the time of use, the tablets were dissolved in 10 ml of an isotonic sodium chloride solution, and the contact lenses to be treated were left in this for about 20–40 min. After this, the cleaning process was complete, and the lenses could be worn again. The tablets can be dissolved in normal tap water as long as the iron content is not too high. In the case of iron-containing water, the tablets may contain conventional physiologically compatible complexing agents in the jacket mixture, in a complexing-effective amount.

We claim:

1. A method for producing a contact lens one-step cleaning and disinfecting tablet designed to be dissolved in water comprising:
(A) preparing a tablettable neutralizing core mixture consisting essentially of at least one biocompatible reducing agent, and/or at least one biocompatible catalyst, and at least one first buffering agent;
(B) forming a core tablet from the mixture of step (A);
(C) preparing a jacket mixture consisting essentially of a biocompatible cleaning and disinfecting agent which is a hydrogen peroxide generating compound and at least one alkylglucoside of the general formula $R_1O(C_nH_{2n}O)_y(Z)_x$ wherein
$R_1$ is a $C_{8-18}$ alkyl,
n is 2 or 3,
y is 0–10,
Z is glucose, and
x is 1–10,
and a second buffering agent; and
(D) enveloping the core tablet of step (B) with the jacket mixture of step (C) so that it is completely surrounded by a stable outer layer thereof.

2. The method of claim 1 wherein step (B) further comprises step (B1) of enveloping said core tablet with a biocompatible and water-soluble lacquer layer.

3. The method of claim 1 wherein step (B) is achieved by compressing the mixture of step (A) under a pressure of about 10,000 kilos per $cm^2$.

4. The method of claim 2 wherein step (B) is achieved by compressing the mixture of step (A) under a pressure of about 10,000 kilos per $cm^2$.

5. The method of claim 2 wherein said enveloping step (B1) is by coating a dense layer of said lacquer on said core tablet utilizing a rotary coating drum.

6. The method of claim 1 wherein step (D) is achieved by (a) pressing a part of said jacket layer into a matrix hole of a tabletting press, (b) introducing said core tablets into said partial layer, and (c) pressing the remainder of said jacket layer on top of the core tablet to produce a completely jacketed tablet.

7. The method of claim 2 wherein step (D) is achieved by (a) pressing a part of said jacket layer into a matrix hole of a tabletting press, (b) introducing said core tablets into said partial layer, and (c) pressing the remainder of said jacket layer on the core tablet to produce a completely jacketed tablet.

8. The method of claim 1 wherein in said core of step (A), said reducing agent is used alone and consists essentially of ascorbic acid, sodium ascorbate, glucose, or a mixture thereof, said reducing agent being present in about 1–5 mol % excess as compared with said at least one biocompatible cleaning and disinfecting agent.

9. The method of claim 1 wherein in said core of step (A), said enzyme catalyst is used alone and consists essentially of catalase, said enzyme being present in about 0.001–0.2 mg/ml based upon the quantity of said biocompatible cleaning and disinfecting agent.

10. The method of claim 1 wherein in said core of step (A), said reducing agent consists essentially of ascorbic acid, sodium ascorbate, glucose, or a mixture thereof, and is present in from one-quarter to one-half of about a 1–5 mol % excess; wherein said enzyme catalyst consists essentially of catalase and is present in about 0.001–0.2 mg/ml, the amounts of both being based upon the quantity of said biocompatible cleaning and disinfecting agent; and wherein said first buffering agent is of a type and present in an amount sufficient to effect a pH of about 7 upon the dissolution of said core.

11. The method of claim 1 wherein in said jacket of step (C), said at least one biocompatible cleaning and disinfecting agent consists essentially of at least one hydrogen peroxide generating compound and sufficient second buffering agent to adjust the pH of an aqueous solution prepared therefrom to about 2–7, both present in an amount sufficient to generate a cleaning and disinfecting effective amount of hydrogen peroxide.

12. The method of claim 1 wherein in said jacket of step (C), said at least one cleaning and disinfecting agent consists essentially of sufficient second buffering agent to adjust the pH of an aqueous solution prepared therefrom to about 2–7, and the average molecular weight ratio of said hydrogen peroxide generating compound to said alkylglucoside is about $1 \cdot 10^2$ to $32 \cdot 10^4$:1, the combination of agents being present in a cleaning and disinfecting effective amount.

13. The method of claim 10 wherein in said jacket of step (C), said at least one cleaning and disinfecting agent consists essentially of sufficient second buffering agent to adjust the pH of an aqueous solution prepared therefrom to about 2–7, and the average molecular weight ratio of said hydrogen peroxide generating compound to said alkylglucoside is about $1 \cdot 10^2$ to $32 \cdot 10^4$:1, the combination of agents being present in a cleaning and disinfecting effective amount.

14. The method of claim 11 wherein in said jacket of step (C), said at least one hydrogen peroxide generating compound consists essentially of urea peroxyhydrate, melamine perhydrate, potassium persulfate, or a mixture thereof, and said second buffering agent consists essentially of citric acid, salicylic acid, lactic acid, or a mixture thereof.

15. The method of claim 1 wherein in said core of step (A), said reducing agent is sodium ascorbate, said catalyst is catalase, and said first buffer is sodium hydrogen carbonate; and wherein in said jacket, said cleaning and disinfecting agent is a combination of urea peroxohydrate and/or melamine perhydrate with at least one alkylglucoside derived from a $C_{12-14}$ fatty acid with an average of 1.4 glucose moieties.

16. The method of claim 15 wherein the ingredients of said core of step (A) and/or said core tablet of step (B) is enveloped in a water-soluble continuously sealed coating of polyvinyl pyrrolidone or a polyacrylate.

17. A contact lens one-step cleaning and disinfecting tablet prepared by the method of claim 1.

18. A contact lens one-step cleaning and disinfecting tablet prepared by the method of claim 2.

19. A contact lens one-step cleaning and disinfecting tablet prepared by the method of claim 3.

20. A contact lens one-step cleaning and disinfecting tablet prepared by the method of claim 4.

21. A contact lens one-step cleaning and disinfecting tablet prepared by the method of claim 5.

22. A contact lens one-step cleaning and disinfecting tablet prepared by the method of claim 6.

23. A contact lens one-step cleaning and disinfecting tablet prepared by the method of claim 7.

24. A contact lens one-step cleaing and disinfecting tablet prepared by the method of claim 8.

25. A contact lens one-step cleaning and disinfecting tablet prepared by the method of claim 9.

26. A contact lens one-step cleaning and disinfecting tablet prepared by the method of claim 10.

27. A contact lens one-step cleaning and disinfecting tablet prepared by the method of claim 11.

28. A contact lens one-step cleaning and disinfecting tablet prepared by the method of claim 12.

29. A contact lens one-step cleaning and disinfecting tablet prepared by the method of claim 13.

30. A contact lens one-step cleaning and disinfecting tablet prepared by the method of claim 14.

31. A contact lens one-step cleaning and disinfecting tablet prepared by the method of claim 15.

32. A contact lens one-step cleaning and disinfecting tablet prepared by the method of claim 16.

* * * * *